United States Patent [19]

Watthey

[11] Patent Number: 4,515,792

[45] Date of Patent: May 7, 1985

[54] TETRACYCLIC HETEROCYCLES AND ANTIDEPRESSANT COMPOSITIONS THEREOF

[75] Inventor: Jeffrey W. H. Watthey, Chappaqua, N.Y.

[73] Assignee: Ciba-Geigy Corporation, Ardsley, N.Y.

[21] Appl. No.: 430,637

[22] Filed: Sep. 30, 1982

[51] Int. Cl.³ .................. C07D 495/14; A61K 31/55
[52] U.S. Cl. .................................. 514/214; 260/243.3
[58] Field of Search ...................... 260/243.3; 427/250

[56] References Cited

U.S. PATENT DOCUMENTS

| | | | |
|---|---|---|---|
| 4,025,513 | 5/1977 | Olivie | 424/250 X |
| 4,062,848 | 12/1977 | Van der Burg | 424/250 X |
| 4,128,641 | 12/1978 | Van der Burg | 424/250 |
| 4,316,900 | 2/1982 | Wasley | 424/250 |
| 4,333,935 | 6/1982 | Van der Burg | 424/250 |

OTHER PUBLICATIONS

Nickolson et al., J. Pharm. Pharmacol. 33, 760, (1981).
Watthey et al., Medicinal Chemistry, vol. 26, 1116–1122, (1983).

*Primary Examiner*—Glennon H. Hollrah
*Assistant Examiner*—D. B. Springer
*Attorney, Agent, or Firm*—Norbert Gruenfeld

[57] ABSTRACT

Tetracyclic heterocycles of the formula

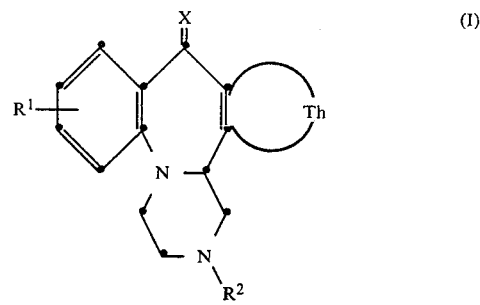

wherein Th is the residue completing a fused thiophen ring, X represents oxo, hydroxyl together with hydrogen, or preferably two hydrogens, $R^1$ represents lower alkyl, lower alkoxy, chloro, bromo, trifluoromethyl or, preferably, hydrogen, and $R^2$ represents hydroxy-lower alkyl, aryl-lower alkyl, or, preferably, lower alkyl, especially methyl, or hydrogen, and therapeutically acceptable acid addition salts thereof are especially useful as antidepressants, in particular in the form of appropriate pharmaceutical compositions. They are obtainable by conventional synthetic methods of organic chemistry.

9 Claims, No Drawings

TETRACYCLIC HETEROCYCLES AND ANTIDEPRESSANT COMPOSITIONS THEREOF

SUMMARY OF THE INVENTION

The invention relates to novel tetracyclic heterocyclic compounds, especially to pyrazinothienobenzazepines of the formula

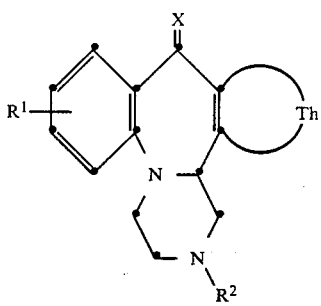

wherein Th represents the divalent radical of the formula —S—CH=CH—, X represents two hydrogens, oxo or hydrogen together with hydroxyl, $R^1$ represents hydrogen, lower alkyl, lower alkoxy, chloro, bromo or trifluoromethyl and $R^2$ represents hydrogen, lower alkyl, hydroxy-lower alkyl or aryl-lower alkyl, and to acid addition salts thereof.

DESCRIPTION OF THE PREFERRED EMBODIMENTS

A lower alkyl as represented by the symbols $R^1$ and $R^2$ has a maximum of 7, and preferably not more than 4 carbon atoms, and can consist of a branched or, preferably, a straight chain, such as, on the one hand, i-propyl, i-butyl, tert-butyl, 2-methylbutyl, 2,2-dimethylpropyl or 2-ethylbutyl, or on the other hand, ethyl, propyl, butyl, pentyl, hexyl, heptyl and, above all, methyl.

A lower alkoxy is derived from a lower alkyl as defined above, especially from a straight-chain alkyl having not more than 4 carbon atoms, and is preferably methoxy.

A hydroxy-lower alkyl is derived from any lower alkyl as defined above, especially from an alkyl having at least 2 carbon atoms. Preferably, the hydroxyl group is not attached to C-1 (i.e. the carbon atom which carries the free valence of the alkyl). Straight-chain hydroxylakyls are preferred, and among them especially those carrying the hydroxyl group at the terminal carbon atom, i.e. ω-hydroxy-lower alkyls, such as, in particular, 5-hydroxypentyl, 4-hydroxybutyl, 3-hydroxypropyl and, above all, 2-hydroxyethyl.

An aryl-lower alkyl is derived from an alkyl having a maximum of 4 carbon atoms, especially from a straight chain alkyl. The component aryl radical can be bicyclic, such as 1- or 2-naphthyl or 1-, 2-, 3- or 4-indenyl, or an analogous radical saturated in one ring, or preferably monocyclic, i.e. phenyl. The aryl radical is preferably attached to the terminal carbon atom of the alkyl chain; correspondingly, the most preferred aryl-lower alkyls are 2-phenylethyl (phenethyl) and, above all, benzyl.

The above compounds of formula I according to the invention can also exist in the form of their acid addition salts. In view of the close relationship between the free compounds and the compounds in the form of their salts, whenever a compound is referred to in this context, a corresponding acid addition salt is also intended, provided such is possible or appropriate under the circumstances. Said acid addition salts are preferably those which are physiologically tolerable, such as salts of inorganic or organic acids which are known to generally afford therapeutically acceptable salts, e.g. strong inorganic acids of the hydrohalic acid type (e.g. hydrochloric or hydrobromic acid) or oxygen-containing inorganic acids (e.g. sulfuric, phosphoric, nitric or perchloric acid) but preferably aliphatic or aromatic carboxylic or sulfonic acids, e.g. formic, acetic, propionic, succinic, glycolic, lactic, malic, tartaric, citric, ascorbic, maleic, fumaric, hydroxymaleic, pyruvic, phenylacetic, benzoic, 4-aminobenzoic, anthranilic, 4-hydroxybenzoic, salicyclic, 4-aminosalicyclic, pamoic, nicotinic, methanesulfonic, ethanesulfonic, hydroxyethanesulfonic, halobenzenesulfonic, toluenesulfonic, naphthalenesulfonic, sulfanilic or cyclohexylsulfamic acid. Also considered are, however, other salts, for example, the picrates, which can be used for purification of the bases obtained.

The compounds of the invention exhibit valuable pharmacological properties, primarily antidepressant activity. It is demonstrable in animal tests using advantageously mammals, e.g. mice, rats, guinea pigs or monkeys, as test objects. Said compounds can be applied to them enterally or parenterally, advantageously orally, or subcutaneously, intravenously or intraperitoneally, for example, within gelatin capsules or in the form of starchy suspensions or aqueous solution respectively. The applied dosage may range between about 0.01 and 100 mg/kg/day, preferably between about 0.5 and 20 mg/kg/day.

Said antidepressant properties of the compounds of the invention are shown in mice by antagonism of clonidine analgesia. In this test system, the compounds of the invention are administered orally or intraperitoneally as aqueous solutions to groups of at least 10 male mice and 30 minutes thereafter 0.1 mg/kg of clonidine is intubated to them orally. 20 minutes later they are injected with 3.75 mg/kg of phenyl-p-benzoquinone intraperitoneally and the number of mice that writhe is counted 5–15 minutes after injection. Any animal writhing is considered indicative of an antidepressant effect and the effective dose of the experimental drug is determined from the number of reactors.

Accordingly, the compounds of the invention are useful antidepressant agents, for example, in the treatment or management of mental depression. They are also useful intermediates in the preparation of other valuable products, especially of pharmacologically active compositions.

Particularly useful for said antidepressant utility are compounds of Formula I, in which $R^1$ is hydrogen, $R_2$ is hydrogen, lower alkyl having not more than 4 carbon atoms, benzyl or 2-hydroxyethyl, X represents two hydrogens, and Th has the meaning given above, both free bases and therapeutically acceptable acid addition salts being applicable.

Outstanding antidepressant compounds of the invention are those of formulae

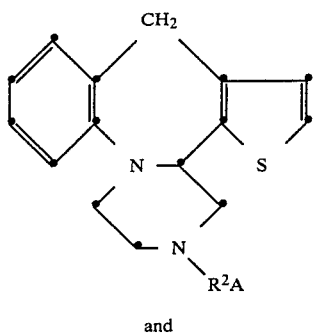

(Ia)

and

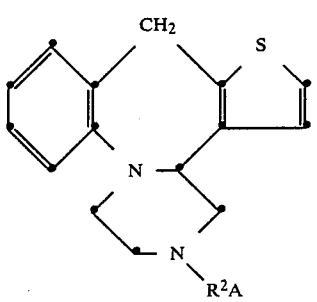

(Ib)

wherein $R^2_A$ is hydrogen or an alkyl having a maximum of 4 carbon atoms, preferably methyl, and therapeutically acceptable acid addition salts thereof.

The invention also relates to the process for the manufacture of the compounds of formulae I, Ia and Ib including acid addition salts thereof. The manufacture is accomplished by processes of chemical synthesis, which are per se known.

Thus, compounds for formula I, wherein X is oxo or two hydrogens can be obtained by cyclization of a piperazine derivative of the formula

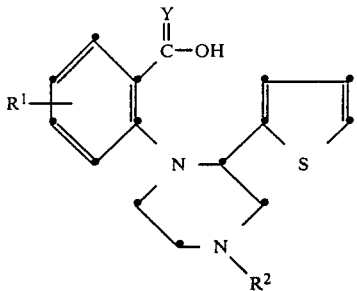

(II)

wherein $R^1$ and $R^2$ have the meanings given hereinabove, and Y represents oxo or two hydrogens, or of an acid addition salt thereof. The cyclization is carried out preferably in the presence of an acid catalyst, e.g. an organic sulfonic acid (such as a lower alkanesulfonic acid, especially methanesulfonic acid, or an arylsulfonic acid, e.g. benzenesulfonic, p-toluenesulfonic, 4-chlorobenzenesulfonic or 4-nitrobenzenesulfonic acid) or a strong inorganic acid, such as a hydrohalic acid (especially hydrochloric or hydrobromic acid) or a conjugate, Lewis-type acid thereof ( such as the conjugate acid of boron trifluoride and hydrofluoric acid or that of aluminum chloride and hydrochloric acid) or a strong oxygen-containing inorganic acid, such as sulfuric, perchloric or any of the phosphoric acids, polyphosphoric acid and lower alkyl, especially ethyl, esters thereof being especially advantageous. The cyclization reaction is analogous both in mechanism and practical aspects (especially in the reaction conditions) to the generally known Friedel-Crafts reaction, the acidic cyclizing agent acting both as dehydration and cyclization catalyst in non-stoichiometric proportions. The cyclization is carried out at temperatures ranging from ambient temperature (about +20° C.) to the boiling point of the reaction mixture (generally not exceeding +150° C.), and aprotic organic solvents are regularly used as reaction medium. Among those, halogenated lower alkanes, such as chloroform or methylene chloride, are especially advantageous, but also $C_5$–$C_{10}$ alkanes and cycloalkanes may be considered. However, the reaction can also be carried out in excess condensing agent as reaction medium, e.g. advantageously in polyphosphoric acid or an ester thereof at elevated temperature, such as at 80° to 120°0 C.,preferably at 100°±5° C.

In order to manufacture a compound of formula I, wherein X represents hydrogen together with hydroxy and the other symbols have the meanings indicated above, the primary cyclization product of formula I, wherein X represents oxo and the other symbols are as indicated above, is treated with a reducing agent conventionally used for the reduction of an oxo group to a hydroxy group. Among the vast number of agents currently available and in general use for this purpose, particular mention should be made of complex hydrides, especially borohydrides (such as sodium and potassium borohydride) and alanates (such as lithium aluminum hydride or sodium aluminum hydride) and related agents in which one or more of the hydrogens are replaced with a residue of an alkanol, alkoxyalkanol or alkanediol. However, also zinc or iron in an acidic medium or electrolytic reduction can be considered as processes of choice.

The starting compounds of general formula II as defined hereinabove are novel; however, they can be prepared by general synthetic processes of organic chemistry, which are conventional per se, e.g. by the reaction sequence which follows: 2-thienylglyoxal can be condensed with ethylenediamine to give rise to 2-(2-thienyl)-piperazine, which in turn can be selectively alkylated, e.g. with one mole equivalent of a corresponding halogenide (e.g. bromide, chloride or iodide) of the formula $R^2$—Hal, wherein Hal is a halogen atom, (especially one mentioned immediately hereinabove) and $R^2$ has the meanings specified in connection with the compounds of formula I, to afford a 1-($R^2$)-3-(2-thienyl)-piperazine. For the preparation of 1-methyl-3-(2-thienyl)-piperazine specifically, an alternative process can be used which involves the condensation of 2-(2-thienyl)-piperazine with ethyl chloroformate and the subsequent reduction of the intermediate ethyl 3-(2-thienyl)-piperazine carboxylate with lithium aluminum hydride in refluxing ether. (In an analogous manner, involving regioselective monoacylation at the nitrogen atom which is more distant from the thienyl, and conventional amide reduction, other intermediates within the above-specified scope of $R^2$ can also be obtained.) The resulting 1-$R^2$-3-(2-thienyl)-piperazine can be in turn condensed (in form of its lithium salt obtained by treatment with e.g. butyl lithium) with 2-(4,4-dimethyl-1,3-oxazolin-2-yl)-methoxybenzene (or with a corresponding compound substituted with $R^1$ of the above-specified meaning in the phenyl ring) of the formula

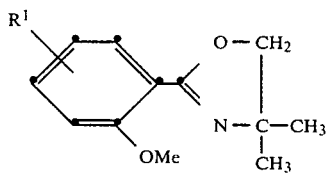

(III)

in which R¹ has the meanings given hereinabove. The condensation product, i.e. a compound of the formula

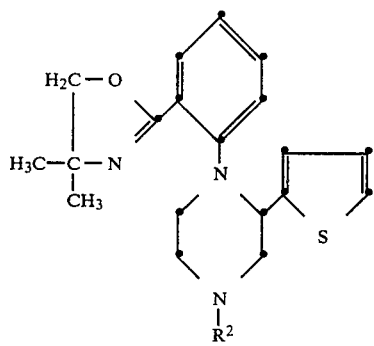

(IV)

wherein R¹ and R² have the meanings given hereinabove, can be smoothly converted into an ester of the acid of formula II wherein Y represents oxo by conventional acid-catalysed alcoholysis. Such an ester can be converted to the desired starting material of formula II by trivial procedures e.g. to the free acid (i.e. a compound of formula II wherein Y is oxo) by hydrolysis, or to the corresponding alcohol (i.e. a compound of formula II wherein Y represents two hydrogens) by a conventional reduction, e.g. with diborane or a complex hydride such as lithium aluminum hydride. This alcohol can also be obtained by reducing, in an analogous manner, the free acid, or a salt, e.g. an alkali metal salt, thereof.

The compound of the invention of formula I so obtained can be converted into other compounds of formula I according to known methods. Thus, for example, those with R² being hydrogen, or alkali metal, e.g. sodium, salts thereof, can be reacted with an alkane epoxide (alkyloxirane) in order to obtain a compound in which R² is hydroxyalkyl, or with an alkylating agent such as with an oxoalkane or oxo-arylalkane under reducing conditions (i.e. by reductive alkylation) or with a reactive ester of a corresponding aliphatic or araliphatic alcohol such as methanol, ethanol or benzyl alcohol respectively e.g. such esterified by a strong inorganic or organic acid, above all a hydrohalic acid (e.g. hydrochloric, hydrobromic or hydriodic acid); sulfuric acid or an aromatic sulfonic acid (e.g. p-toluene- or m-bromobenzenesulfonic acid) in order to obtain the corresponding N-substituted compounds of formula I wherein R² is lower alkyl or lower aralkyl as defined hereinabove.

Conversely, resulting compounds according to the invention of formula I wherein R² is different from hydrogen can be converted into a compound of formula I wherein R² represents hydrogen by conventional procedures, e.g. by catalytic hydrogenolysis of such a compound of formula I in which R² is an aralkyl having the aryl radical in the alpha-position (such as benzyl or 1-phenylethyl), or by elimination of a lower alkyl, especially methyl, by treating a compound of formula I wherein R² is lower alkyl or hydroxy-lower alkyl (and, in particular, methyl) with a lower alkyl chloroformate, e.g. ethyl chloroformate, and hydrolysing the intermediate compound of formula I wherein R is lower alkoxycarbonyl; a base-catalysed hydrolysis, e.g. with an aqueous solution of alkali metal hydroxides or carbonates, being preferred.

The compounds of the invention are either obtained in the free, basic form, or as a salt thereof. Any resulting base can be converted into a corresponding acid addition salt, preferably with the use of an acid or anion exchange preparation, or resulting salts can be converted into the corresponding free bases, for example, with the use of a stronger base, such as a metal or ammonium hydroxide, or a basic salt e.g. an alkali metal hydroxide or carbonate, or a cation exchanger. Some salts, for example, the picrates, can be used for purification of the bases obtained; the bases are converted into salts, the salts are separated, and the bases are liberated from the salts.

In case mixtures of geometrical or optical isomers of the above compounds, e.g. those of formulae I, II, or IV, are obtained, they can be separated into the single isomers by methods in themselves knows, e.g. by fractional distillation, crystallization and/or chromatography. Racemic products can likewise be resolved into the antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or other agents respectively and/or inert atmospheres, at low temperatures, room temperature or elevated temperatures, preferably at the refluxing temperature of the mixture, at atmospheric or superatmospheric pressure.

The invention further includes any variant of the present process, in which an intermediate product obtainable at any stage of the process is utilized as starting material, and only the remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, saccharose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, stach paste, gelatin, tragacanth, methylcellulose, sodium carboxymethylcellulose and/or polyvinylpyrrolidone, if desired, (d) disintegrants, e.g. starches, agar, alginic acid or its sodium salt, or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

The following examples are intended to illustrate the invention and are not to be construed as being limitations thereon. Temperatures are given in degrees Centigrade, and all parts whereever given are parts by weight. If not mentioned otherwise, all evaporations are performed under reduced pressure, preferably between about 15 and 100 mm Hg.

PREPARATION 1

2-(2-Thienyl)Piperazine

A solution of ethylenediamine (4.1 g, 0.068 mol) in ethanol (25 ml) is added dropwise to a solution of 2-thienylglyoxal hydrate [prepared by the procedure of F. Kipnis and J. Ornfelt, J. Amer. Chem. Soc. 68, 2734 (1946)] (10.0 g, 0.063 mol) in ethanol (250 ml) at 0° C. under an atmosphere of dry nitrogen. The cooling bath is removed and the reaction mixture stirred for an additional 1.5 h. Sodium borohydride (4.5 g, 0.126 mol) is added all at once, and a cooling bath used to control the exothermic reaction. Stirring is continued for an additional 18 h. Water (25 ml) is added, and the ethanol removed under reduced pressure. The remaining aqueous solution is extracted with methylene chloride (3×100 ml) and the extracts dried with potassium carbonate. Removal of the solvent under reduced pressure gives 2-(2-thienyl)piperazine as an off-white solid. An analytical sample is obtained by addition of an ethereal solution of the base to an ethereal solution of oxalic acid dihydrate. The resulting precipitate is washed with diethyl ether and methanol, and the free base (m.p. 81°–83° C.) is obtained with a saturated solution of potassium carbonate.

PREPARATION 2

Ethyl 3-(2-Thienyl)Piperazine-1-Carboxylate

A solution of ethyl chloroformate (20.4 g, 0.19 mol) in acetic acid (150 ml) is added dropwise with stirring to a solution of 2-(2-thienyl)-piperazine (31.6 g, 0.19 mol; Preparation 1) in acetic acid (150 ml) at 65° C. under an atmosphere of dry nitrogen. After 1 h, the solution is allowed to cool to room temperature, and stirring is maintained for an additional 16 h. The reaction mixture is added to chilled 10N NaOH (750 ml) and ice is added to control the exothermic reaction. The mixture is extracted with methylene chloride (4×300 ml), the organic solution is dried(potassium carbonate), and the solvent removed under reduced pressure to give the carbamate (30.0 g) as a light brown oil. This material is dissolved in methanol (250 ml), and the solution added to a solution of maleic acid (18.6 g; 1 eq) in methanol (250 ml). The mixture is treated with charcoal and the solvent removed under reduced pressure to give an oil which crystallizes on trituration with ethyl acetate. The maleate salt melts at 165°–166° C.

PREPARATION 3

1-Methyl-3-(2-thienyl)Piperazine

A solution of ethyl 3-(2-thienyl)piperazine-carboxylate (27.2 g, 0.11 mol; Preparation 2) in diethyl ether (300 ml) is added to a stirred suspension of lithium aluminum hydride (10.8 g, 0.28 mol) in diethyl ether (1300 ml). The mixture is refluxed for 12 h, cooled to room temperature and worked up as described in "Reagents for Organic Synthesis", Fieser, L. F. and Fieser, M., John Wiley and Sons, Inc., New York, N.Y. 1967, p. 583. The ether solution is dried (potassium carbonate) and evaporated to give 1-methyl-3-(2-thienyl)piperazine as a light yellow oil, which is characterized as the maleate salt (m.p. 123°–124.5° C.), which is prepared in the manner described in Preparation 2.

PREPARATION 4

1-[2-(4,4-dimethyl-1,3-oxazolin-2-yl)phenyl]-4-methyl-2-(2-thienyl)piperazine A solution of 1-methyl-3-(2-thienyl) piperazine (8.5 g; 0.046 mole, Preparation 3) in dry tetrahydrofuran (60 ml) is cooled to −78 C. under an atmosphere of dry nitrogen. N-Butyllithium in hexane (18 ml of a 2.6N solution) is added to the stirred solution during 5 min. The temperature of the resulting suspension is raised to 0 C. and stirring is maintained for 0.5 h. A solution of 2-(4,4-dimethyl-1,3-oxazolin-2-yl)anisole [prepared as described by A. I. Meyers and E. D. Mihelich, J. Amer. Chem. Soc., 97, 7383 (1975)] (9.5 g; 0.046 mol) in dry tetrahydrofuran (90 ml) is added during 45 min. The reaction mixture becomes dark. Stirring is continued for an additional 1 h. at 0 C. and then at room temperature for 18 h. Water (15 ml) is added and the solvent removed under reduced pressure. The residue is partitioned between diethyl ether (150 ml) and water (75 ml). The aqueous phase is extracted with ether (2×50 ml) and the combined organic solutions washed with saturated aqueous solution of potassium carbonate (75 ml) and dried (potassium carbonate). The solvent is removed under reduced pressure and the residue washed with petroleum ether (100 ml) to give the title N-arylpiperazine. An analytical sample is obtained by recrystallization from petroleum ether, m.p. 114°–115° C.

PREPARATION 5

1-(2-Carbethoxyphenyl)-4-methyl-2-(2-thienyl)piperazine

A solution of the oxazoline described in Preparation 4 (33.1 g, 0.090 mol) in ethanolic sulfuric acid (2.2 L of a 1.5N-Solution) is refluxed for 12 h. Approximately 75% of the ethanol is removed under reduced pressure and the remaining solution is poured into a saturated solution of potassium carbonate (1000 ml). This solution is extracted with methylene chloride (4×350 ml) and the extracts dried(potassium carbonate) and evaporated. The resulting oil is purified by column chromatography using silica gel (600 g; ethyl acetate as solvent). The title ester is isolated as a major component. For characterization, the maleate salt is prepared in the manner given in preparation 2, m.p. 145°–145° C.

PREPARATION 6

1-(2-Hydroxymethylphenyl)-4-methyl-2-(2-thienyl)piperazine

A solution of the ester described in Preparation 5 (10.7 g, 0.032 mol) in diethyl ether (225 ml) is added to a stirred suspension of lithium aluminum hydride (3.9 g, 0.097 mol) in diethyl ether (150 ml). The reaction mixture is refluxed for 12 h., cooled to room temperature and worked up as described in Preparation 3. The resulting colorless oil crystallizes to give the title alcohol in a high state of purity, m.p. 81°–83° C.

EXAMPLE 1

1,2,3,4,10,13b-Hexahydro-2-methylpyrazino[1,2-a]thieno[2,3-c]-[1]benzazepine and the corresponding [3,2-c] isomer.

A solution of 1-(2-hydroxymethylphenyl)-4-methyl-2-(2-thienyl)piperazine (4.7 g, 0.016 mol) and ethyl polyphosphate ("polyphosphate ester") (93 g) in methylene chloride (930 ml) is refluxed for 12 h. The solution is cooled to room temperature and the precipitated solid filtered off. This material is partitioned between methylene chloride (300 ml) and saturated aqueous ammonia (300 ml). The aqueous phase is extracted with methylene chloride (2×75 ml), and the combined organic solutions washed with 100 ml of a saturated sodium chloride solution and dried ($K_2CO_3$). Evaporation of the solvent gives an oil, which is chromatographed on silica gel. Elution with ethyl acetate gives two discrete fractions: Fraction 1 (1,2,3,4,10,13b-hexahydro-2-methylpyrazino[1,2-a]thieno[2,3-c]-[1]benzazepine) has an $R_f$ of 0.2 on TLC (solvent: ethyl acetate), characterized as the maleate, m.p. 187°–188.5° C.; and Fraction 2, which is the [3,2-c] isomer, characterized as the fumarate, m.p. 198°–201° C. The mass spectra of the two isomers are essentially identical: m/e (relative intensity) 270 (M+, 100), 226 (22), 199 (63), 72 (70).

The starting piperazine derivative is prepared by the reaction sequence given in Preparations 1 to 6.

EXAMPLE 2

Preparation of 10,000 tablets each containing 5 mg of the active ingredient

| Formula: | |
| --- | --- |
| 1,2,3,4,10,13b-Hexahydro-2-methyl-pyrazino[1,2-a]thieno[2,3-c]-[1]benzazepine Maleate | 50.00 g |
| Lactose | 1,157.00 g |
| Corn Starch | 75.00 g |
| Polyethylene Glycol 6,000 | 75.00 g |
| Talcum Powder | 75.00 g |
| Magnesium Stearate | 18.00 g |
| Purified Water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35° C., broken on a screen with 1.2 mm openings and compressed into tablets using concave punches with 6.4 mm diameter, uppers bisected. Analogously, tablets are prepared from the same amount of the [3,2-c] isomer of the active ingredient (cf. Example 1).

EXAMPLE 3

Preparation of 10,000 capsules each containing 10 mg of the active ingredient;

| Formula: | |
| --- | --- |
| 1,2,3,4,10,13b-hexahydro-2-methylpyrazino[1,2-a]thieno[3,2-c]-[1]benzazepine Fumarate | 100.00 g |
| Lactose | 1,800.0 g |
| Talcum powder | 100.0 g |

Procedure

All the powders are passed through a screen with openings of 0.6 mm. Then the drug substance is placed in a suitable mixer and mixed first with the talcum, then with the lactose until homogeneous. No. 3 capsules are filled with 200 mg, using a capsule filling machine.

Analogously, capsules are prepared from the same amount of the [2,3-c] isomer of the active ingredient (cf. Example 1).

What is claimed is:

1. A pyrazinothienobenzazepine of the general formula

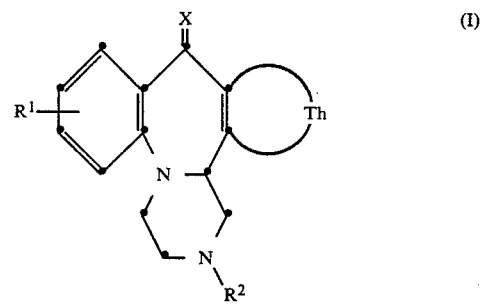

wherein Th represents the divalent radical of the formula —S—CH=CH—, X represents two hydrogens, oxo or hydrogen together with hydroxy, $R^1$ represents hydrogen, lower alkyl, lower alkoxy, chloro, bromo or trifluoromethyl, and $R^2$ represents hydrogen, lower alkyl, hydroxy-lower alkyl or aryl-lower alkyl, or an acid addition salt thereof.

2. A compound according to claim 1 of formula I wherein Th has the meaning specified in claim 1, X represents two hydrogens, $R^1$ is hydrogen, and $R^2$ is hydrogen, alkyl having a maximum of 4 carbon atoms, benzyl or 2-hydroxyethyl, or a therapeutically acceptable acid addition salt thereof.

3. A compound according to claim 1 of the formula

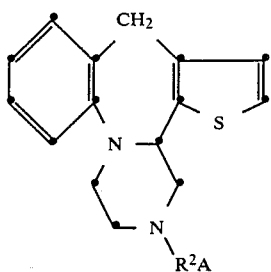 (Ia)

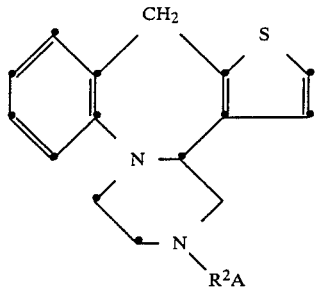 (Ib)

wherein $R^2_A$ is hydrogen or alkyl having a maximum of 4 carbon atoms, or a therapeutically acceptable acid addition salt thereof.

4. A compound according to claim 3 which compound is 1,2,3,4,10,13b-hexahydro-2-methyl-pyrazino[1,2-a]thieno[2,3,-c][1]-benzazepine of the formula Ia wherein $R^2_A$ is methyl, or a therapeutically acceptable acid addition salt thereof.

5. A compound according to claim 4 which compound is the maleate salt of 1,2,3,4,10,13b-hexahydro-2-methylpyrazino-[1,2-a]thieno[2,3-c][1]benzazepine.

6. A compound according to claim 1 of the formula wherein $R^2_A$ is hydrogen or an alkyl having a maximum of 4 carbon atoms, or a therapeutically acceptable acid addition salt thereof.

7. A compound according to claim 6 which compound is 1,2,3,4,10,13b-hexahydro-2-methyl-pyrazino[1,2-a]thieno[3,2-c] [1]benzazepine of formula Ib wherein $R^2_A$ is methyl, or a therapeutically acceptable acid addition salt thereof.

8. A compound according to claim 7 which compound is the fumarate salt of 1,2,3,4,10,13b-hexahydro-2-methylpyrazino[1,2-a]thieno[3,2-c][1]benzazepine.

9. An antidepressant pharmaceutical composition comprising an antidepressively effective amount of a compound as claimed in claim 1 together with a pharmaceutical excipient.

* * * * *